(12) United States Patent
Re (10) Patent No.: US 8,298,239 B2
(45) Date of Patent: Oct. 30, 2012

(54) TIBIAL GUIDE FOR ACL REPAIR HAVING INTERCHANGEABLE AND/OR ROTATABLE OUTRIGGER

(75) Inventor: Paul Re, Boston, MA (US)

(73) Assignee: Tyco Healthcare Group LP, Mansfield, MA (US)

( * ) Notice: Subject to any disclaimer, the term of this patent is extended or adjusted under 35 U.S.C. 154(b) by 90 days.

(21) Appl. No.: 12/548,630

(22) Filed: Aug. 27, 2009

(65) Prior Publication Data

US 2010/0049196 A1    Feb. 25, 2010

Related U.S. Application Data

(63) Continuation-in-part of application No. 12/367,007, filed on Feb. 6, 2009.

(60) Provisional application No. 61/066,572, filed on Feb. 21, 2008.

(51) Int. Cl.
*A61B 17/56* (2006.01)
*A61B 17/64* (2006.01)

(52) U.S. Cl. .......................... 606/88; 606/87

(58) Field of Classification Search ............. 606/87–89, 606/96; 623/13.11
See application file for complete search history.

(56) References Cited

U.S. PATENT DOCUMENTS

| 4,535,768 | A | | 8/1985 | Hourahane et al. |
|---|---|---|---|---|
| 4,672,957 | A | | 6/1987 | Hourahane |
| 4,708,139 | A | | 11/1987 | Dunbar, IV |
| 4,739,751 | A | | 4/1988 | Sapega et al. |
| 4,781,182 | A | | 11/1988 | Purnell et al. |
| 4,823,780 | A | | 4/1989 | Odensten et al. |
| 4,883,048 | A | | 11/1989 | Purnell et al. |
| 4,901,711 | A | | 2/1990 | Goble et al. |
| 4,920,958 | A | | 5/1990 | Walt et al. |
| 4,945,904 | A | | 8/1990 | Bolton et al. |
| 5,112,335 | A | | 5/1992 | Laboureau et al. |
| 5,112,337 | A | | 5/1992 | Paulos et al. |
| 5,139,520 | A | | 8/1992 | Rosenberg et al. |
| 5,154,720 | A | | 10/1992 | Trott et al. |
| 5,163,940 | A | * | 11/1992 | Bourque .................. 606/96 |
| 5,250,055 | A | | 10/1993 | Moore et al. |
| 5,269,786 | A | * | 12/1993 | Morgan .................. 606/96 |

(Continued)

FOREIGN PATENT DOCUMENTS

CA        2654485        8/2009

(Continued)

OTHER PUBLICATIONS

PCT International Search Reports dated Oct. 12, 2010 for the corresponding application PCT/US2010/046351, Oct. 12, 2010 for the corresponding application PCT/US2010/046359, Oct. 19, 2010 for the corresponding application PCT/US2010/046373, and Oct. 26, 2010 for the corresponding application PCT/US2010/046366.

(Continued)

*Primary Examiner* — Kevin T Truong
*Assistant Examiner* — Zade Coley (57) ABSTRACT

A device for positioning a tibial tunnel during ACL reconstruction, the device comprising: a distal portion including a body and a distal arm extending from the distal end of the body, and an outrigger configured to be held by a user. The outrigger and the distal portion are selectively rotatable relative to each other such that the distal portion and the outrigger may be selectively moved out of alignment relative to each other when viewed from above.

12 Claims, 12 Drawing Sheets

U.S. PATENT DOCUMENTS

| | | | |
|---|---|---|---|
| 5,300,077 A | 4/1994 | Howell | |
| 5,320,115 A | 6/1994 | Kenna | |
| 5,350,383 A * | 9/1994 | Schmieding et al. | 606/96 |
| 5,374,269 A | 12/1994 | Rosenberg | |
| 5,409,494 A | 4/1995 | Morgan | |
| 5,458,602 A | 10/1995 | Goble et al. | |
| 5,464,407 A | 11/1995 | McGuire | |
| 5,520,694 A * | 5/1996 | Dance et al. | 606/86 R |
| 5,562,664 A * | 10/1996 | Durlacher et al. | 606/96 |
| 5,562,669 A | 10/1996 | McGuire | |
| 5,570,706 A * | 11/1996 | Howell | 128/898 |
| 5,613,971 A | 3/1997 | Lower et al. | |
| 5,643,273 A * | 7/1997 | Clark | 606/96 |
| 5,681,320 A * | 10/1997 | McGuire | 606/104 |
| 5,688,284 A * | 11/1997 | Chervitz et al. | 606/96 |
| 5,743,909 A * | 4/1998 | Collette | 606/88 |
| 5,891,150 A * | 4/1999 | Chan | 606/96 |
| 5,968,050 A * | 10/1999 | Torrie | 606/87 |
| 6,019,767 A * | 2/2000 | Howell | 606/96 |
| 6,120,511 A | 9/2000 | Chan | |
| 6,254,604 B1 | 7/2001 | Howell | |
| 6,254,605 B1 | 7/2001 | Howell | |
| 6,264,694 B1 * | 7/2001 | Weiler | 623/13.14 |
| 6,280,472 B1 | 8/2001 | Boucher et al. | |
| 6,306,138 B1 | 10/2001 | Clark et al. | |
| 6,499,486 B1 | 12/2002 | Chervitz et al. | |
| 6,764,513 B1 | 7/2004 | Dowling | |
| 6,958,067 B2 | 10/2005 | Whittaker et al. | |
| 7,025,786 B2 | 4/2006 | Goble et al. | |
| 7,063,724 B2 | 6/2006 | Re et al. | |
| 7,131,974 B2 | 11/2006 | Keyer et al. | |
| 7,229,448 B2 | 6/2007 | Goble et al. | |
| 7,238,189 B2 | 7/2007 | Schmieding et al. | |
| 7,326,247 B2 | 2/2008 | Schmieding et al. | |
| 7,458,975 B2 | 12/2008 | May et al. | |
| 7,473,267 B2 | 1/2009 | Nguyen et al. | |
| 7,520,898 B2 | 4/2009 | Re et al. | |
| 7,527,648 B2 | 5/2009 | May et al. | |
| 7,575,578 B2 | 8/2009 | Wetzler et al. | |
| 7,578,824 B2 | 8/2009 | Justin et al. | |
| 7,594,917 B2 | 9/2009 | Whittaker et al. | |
| 2002/0133165 A1 | 9/2002 | Whittaker et al. | |
| 2003/0009173 A1 | 1/2003 | McGuire et al. | |
| 2003/0050642 A1 | 3/2003 | Schmieding | |
| 2003/0065391 A1 | 4/2003 | Re et al. | |
| 2003/0191530 A1 | 10/2003 | Sklar | |
| 2004/0106928 A1 | 6/2004 | Ek | |
| 2004/0172034 A1 | 9/2004 | Re et al. | |
| 2004/0199166 A1 | 10/2004 | Schmieding et al. | |
| 2004/0254585 A1 | 12/2004 | Whittaker et al. | |
| 2005/0234469 A1 | 10/2005 | Whittaker et al. | |
| 2006/0074434 A1 | 4/2006 | Wenstrom, Jr. et al. | |
| 2006/0265064 A1 | 11/2006 | Re et al. | |
| 2006/0271059 A1 * | 11/2006 | Reay-Young et al. | 606/96 |
| 2006/0293689 A1 | 12/2006 | Miller et al. | |
| 2007/0123902 A1 | 5/2007 | Berberich et al. | |
| 2007/0191853 A1 | 8/2007 | Stone | |
| 2007/0203499 A1 | 8/2007 | Boucher et al. | |
| 2007/0213819 A1 | 9/2007 | McKernan et al. | |
| 2007/0233128 A1 | 10/2007 | Schmieding et al. | |
| 2007/0233151 A1 * | 10/2007 | Chudik | 606/96 |
| 2007/0250067 A1 | 10/2007 | Schmieding et al. | |
| 2007/0270857 A1 | 11/2007 | Lombardo et al. | |
| 2008/0103506 A1 | 5/2008 | Volpi et al. | |
| 2008/0119929 A1 | 5/2008 | Schmieding et al. | |
| 2008/0140197 A1 | 6/2008 | Goble et al. | |
| 2008/0188935 A1 | 8/2008 | Saylor et al. | |
| 2008/0234819 A1 | 9/2008 | Schmieding et al. | |
| 2009/0018654 A1 | 1/2009 | Schmieding et al. | |
| 2009/0030417 A1 | 1/2009 | Takahashi | |
| 2009/0171355 A1 | 7/2009 | Amis et al. | |
| 2009/0187244 A1 | 7/2009 | Dross | |
| 2009/0216236 A1 | 8/2009 | Re | |

FOREIGN PATENT DOCUMENTS

| | | |
|---|---|---|
| CA | 2654486 | 8/2009 |
| EP | 2092900 | 8/2009 |
| FR | 2716364 A1 * | 8/1995 |
| FR | 2744621 | 8/1997 |
| WO | WO 99/29237 | 6/1999 |

OTHER PUBLICATIONS

PCT International Search Report dated Oct. 19, 2010 for corresponding application PCT/US2010/046764.

PCT International Search Report dated Oct. 25, 2010 for corresponding application PCT/US2010/046774.

PCT International Search Report dated Oct. 26, 2010 for corresponding application PCT/US2010/046769.

PCT International Search Report dated Oct. 27, 2010 for corresponding application PCT/US2010/046804.

* cited by examiner

TIBIAL GUIDE FOR ACL REPAIR HAVING INTERCHANGEABLE AND/OR ROTATABLE OUTRIGGER

CROSS REFERENCE TO RELATED APPLICATIONS

This application is a continuation-in part of, and claims the benefit of priority to, U.S. patent application Ser. No. 12/367,007, filed Feb. 6, 2009, entitled "Device for Orienting the Tibial Tunnel Position During an ACL Reconstruction" and U.S. Provisional Patent Application Ser. No. 61/066,572, filed Feb. 21, 2008, entitled "Device for Orienting the Tibial Tunnel Position During an ACL Reconstruction," the disclosures of each being incorporated herein by reference in their entirety. In addition, this application is related to U.S. Provisional Patent Application Ser. No. 61/066,575, filed Feb. 21, 2008, entitled "Guide for Creating a Femoral Tunnel During an ACL Reconstruction" and U.S. patent application Ser. No. 12/366,967, filed Feb. 6, 2009, entitled "Guide for Creating a Femoral Tunnel During an ACL Reconstruction," the disclosures of each also being incorporated herein by reference in their entirety.

BACKGROUND

1. Technical Field

This invention relates to surgical apparatus and procedures in general, and more particularly to surgical apparatus and procedures for reconstructing a ligament.

2. Background of Related Art

A ligament is a piece of fibrous tissue which connects one bone to another. Ligaments are frequently damaged (e.g., detached or torn or ruptured, etc.) as the result of injury and/or accident. A damaged ligament can cause instability, impede proper motion of a joint and cause pain. Various procedures have been developed to repair or replace a damaged ligament. The specific procedure used depends on the particular ligament which is to be restored and on the extent of the damage.

Figure 1:
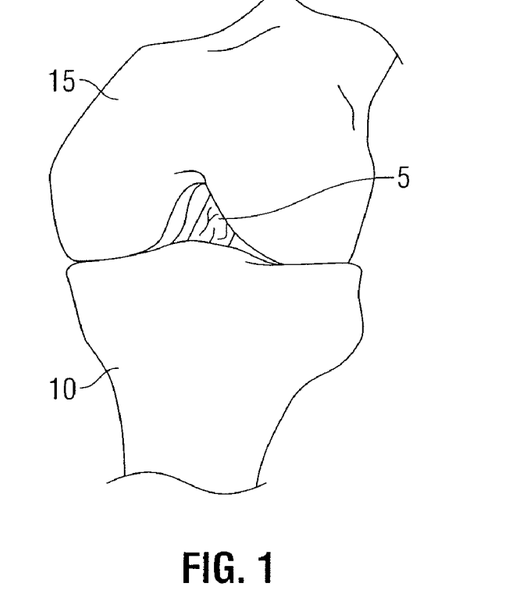
FIG. 1 is a perspective view of a knee joint showing an ACL.
Figure 2:
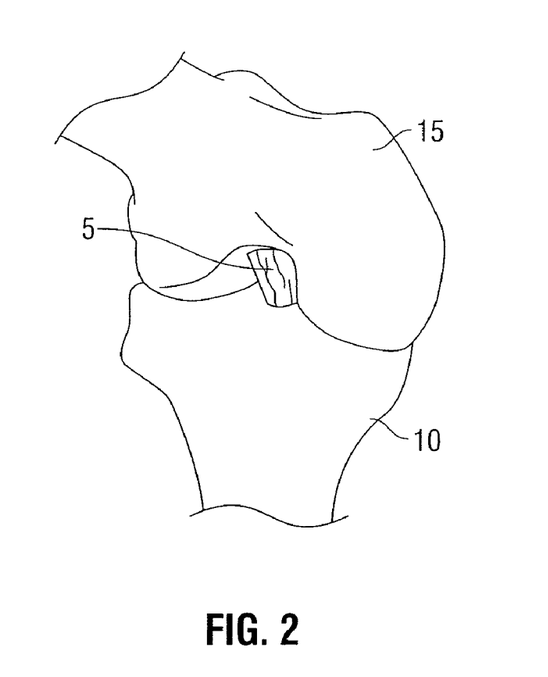
FIG. 2 is an alternate perspective view of the knee joint of FIG. 1.

One ligament which is frequently damaged as the result of injury and/or accident is the anterior cruciate ligament (i.e., the ACL). Looking first at FIGS. 1 and 2, it will be seen that the ACL 5 extends between the top of the tibia 10 and the bottom of the femur 15. A damaged ACL can cause instability of the knee joint and cause substantial pain and arthritis. For this reason, ACL reconstruction is a common procedure with more than 100,000 cases being performed in the United States annually.

Figure 3:
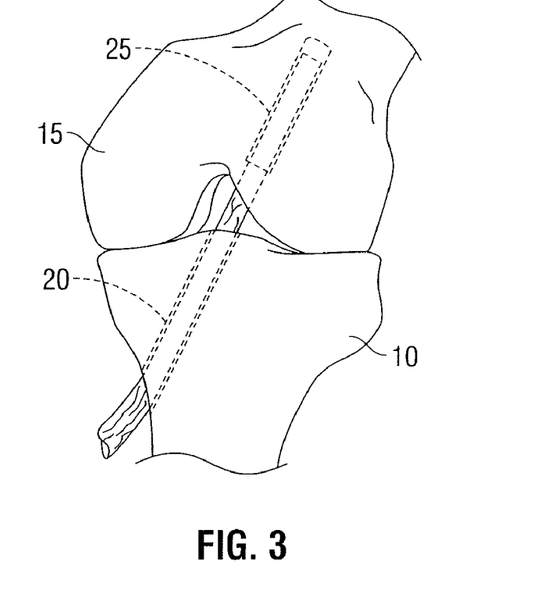
FIG. 3 is a perspective view of a knee joint including tibial and femoral tunnels (shown in phantom) and a ligament graft.

Various procedures have been developed to restore and/or reconstruct a damaged ACL through a graft ligament replacement. Traditionally, this procedure is performed utilizing a trans-tibial approach. In this approach, a bone tunnel 20 (FIG. 3) is first drilled up through tibia 10. Tibial tunnel 20 is then used to access the interior of the knee joint, and it is from tibial tunnel 20 that the position of a femoral tunnel 25 is determined. In this respect, it should be appreciated that the proper positioning of femoral tunnel 25 is important and that numerous guides have been designed to ensure that tibial tunnel 20 is correctly positioned in order to properly position the resulting femoral tunnel 25.

Figure 4:
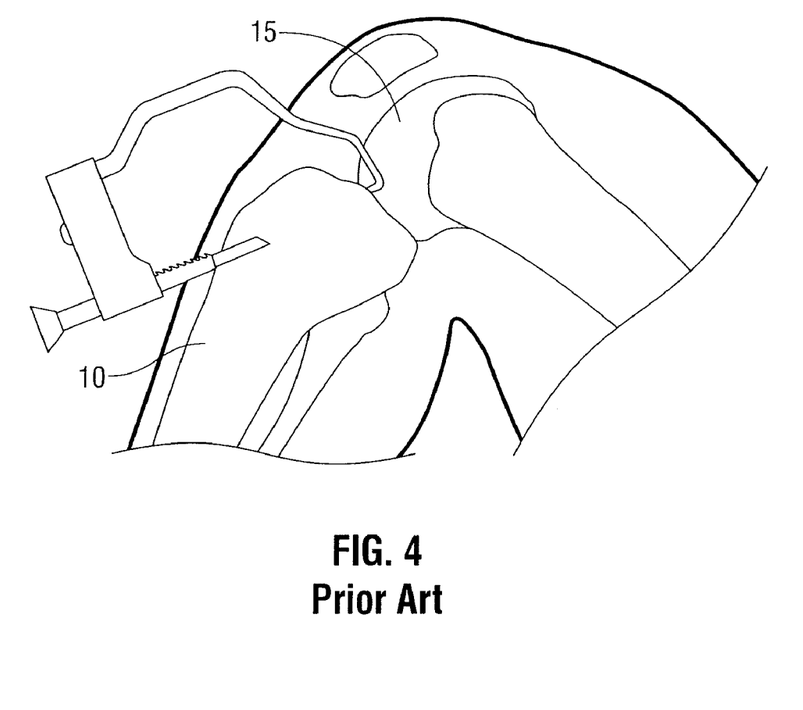
FIGS. 4-8 are views of various prior art embodiments of tibial tunnel positioning guides.
Figure 5:
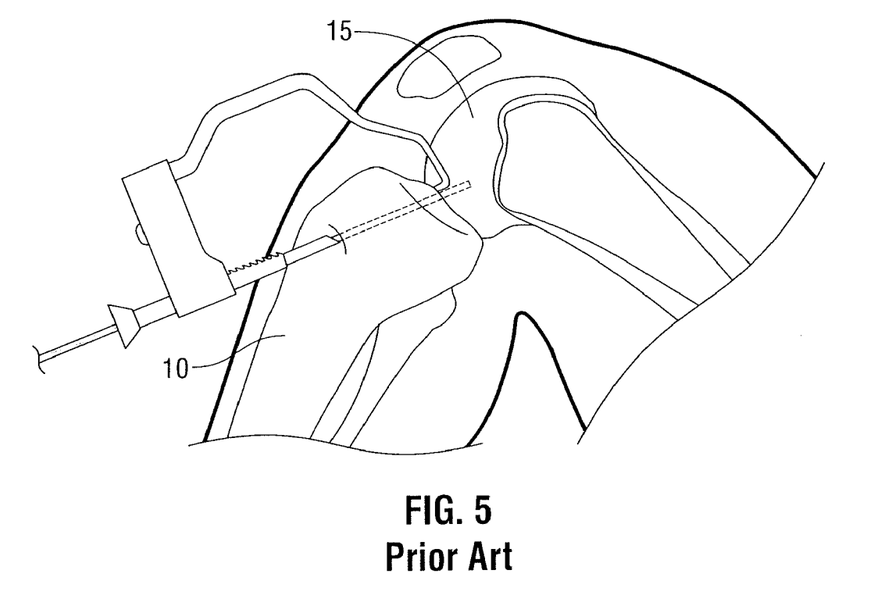
Figure 6:
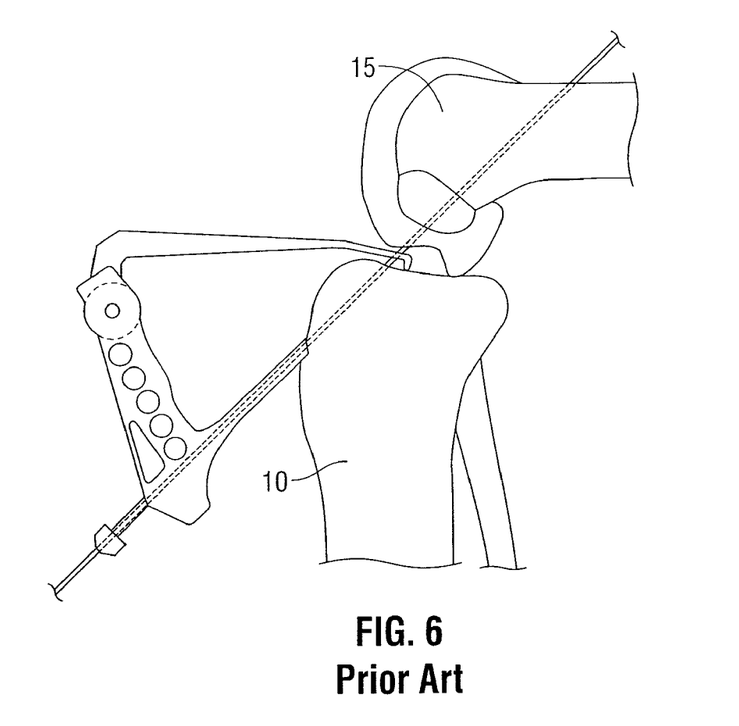
Figure 7:
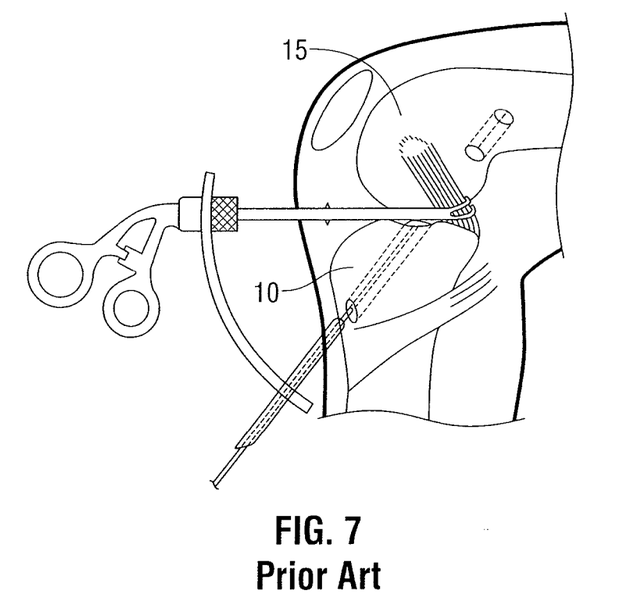

Looking next at FIGS. 4, 5 and 6, simple tibial tunnel positioning guides generally consist of a hooked tip that may be positioned along the ACL footprint on the tibia at a position chosen by the surgeon. Other tibial tunnel positioning guides are more constraining, in order to attempt to obtain a more reliable and reproducible position for the tibial tunnel. As shown in FIG. 7, some other tibial tunnel positioning guides reference the tibial base of the posterior cruciate ligament ("PCL") (U.S. Pat. No. 5,409,494 to Morgan et al.).

Figure 8:
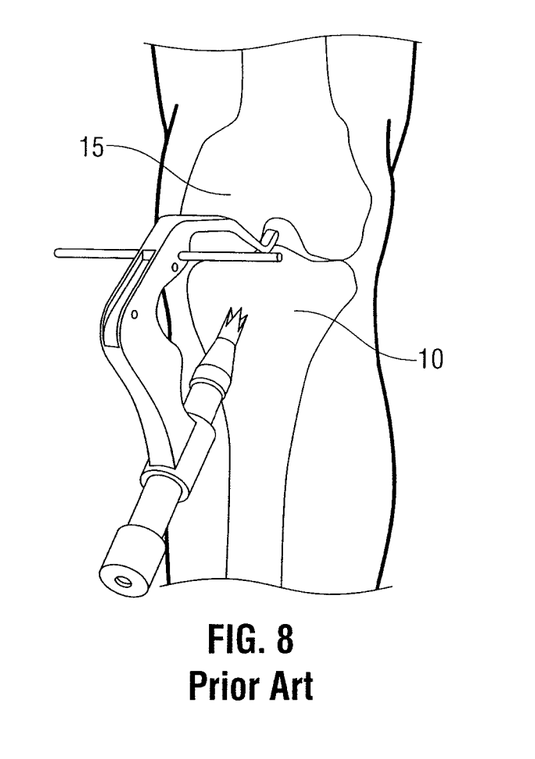
Figure 9:
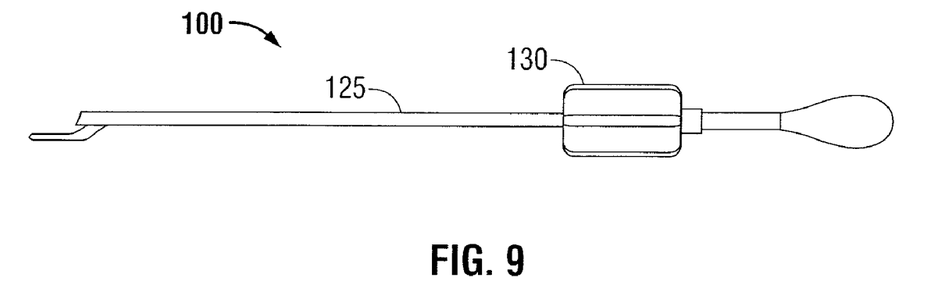
FIG. 9 is a femoral guide for use in ACL reconstruction utilizing the medial portal approach.
Figure 10:
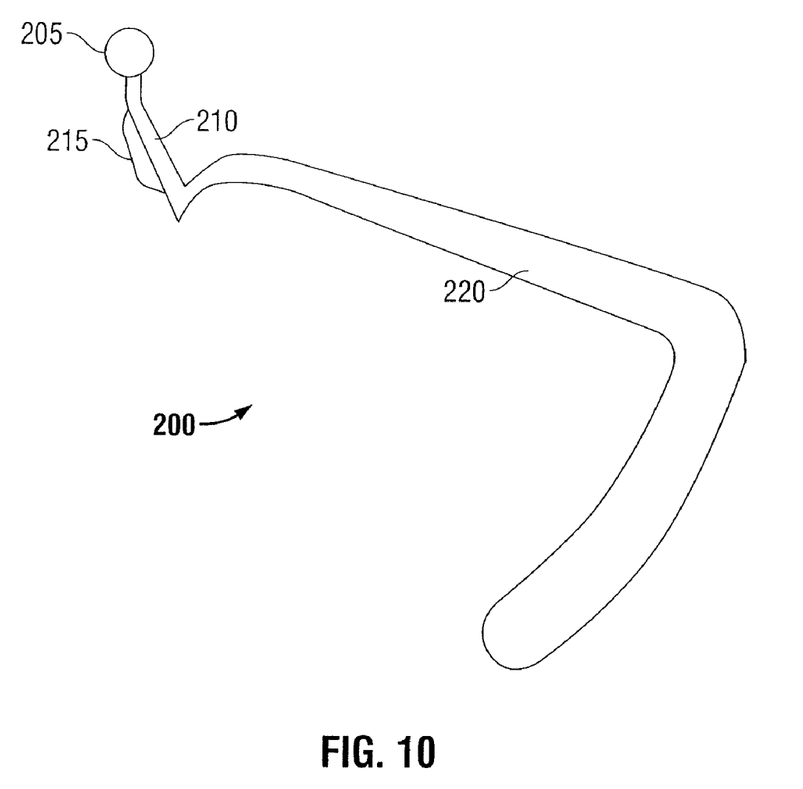
FIG. 10 is a side view of a tibial tunnel positioning guide according to an embodiment of the present disclosure.
Figure 11:
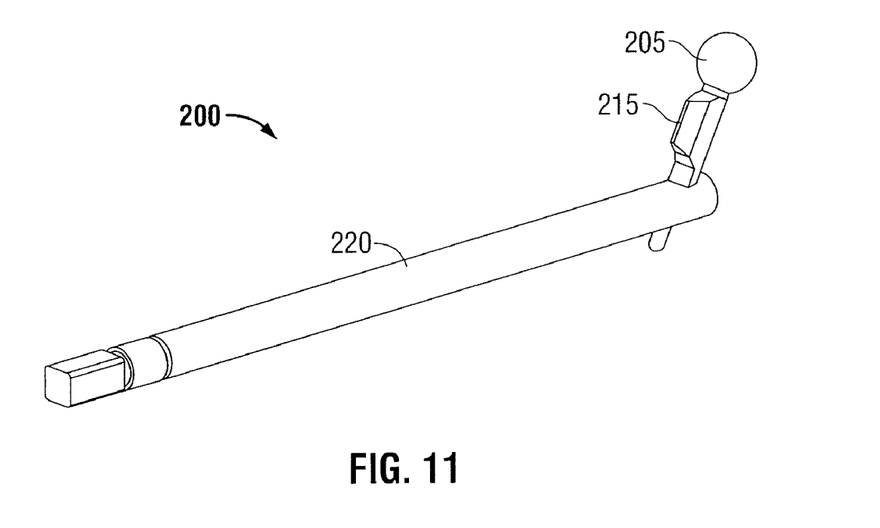
FIG. 11 is a perspective view of a tibial tunnel positioning guide according to an alternative embodiment of the present disclosure.
Figure 12:
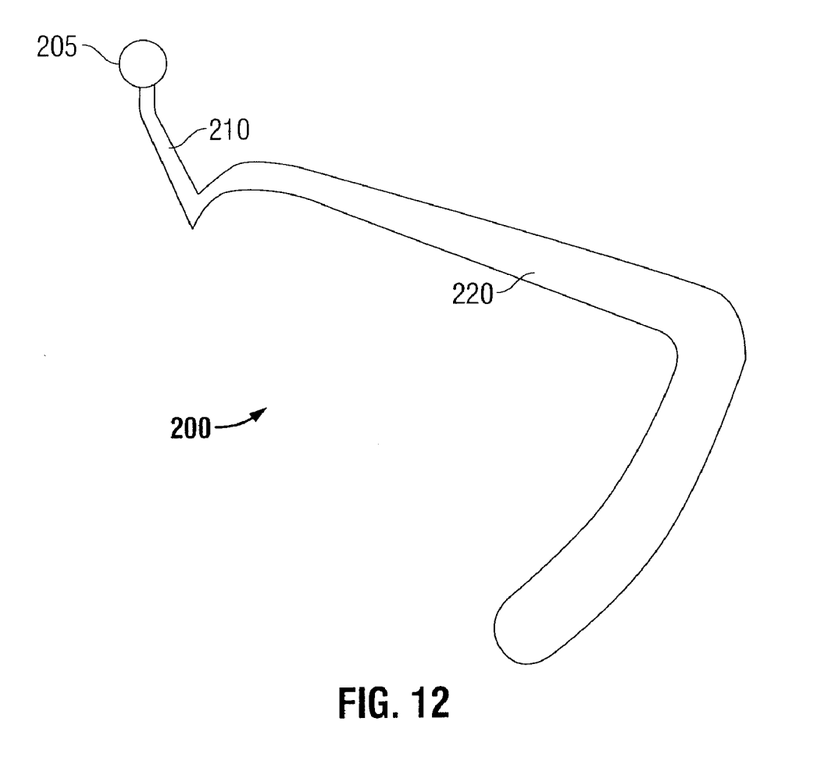
FIG. 12 is a side view of a tibial tunnel positioning guide according to another embodiment of the present disclosure.
Figure 13:
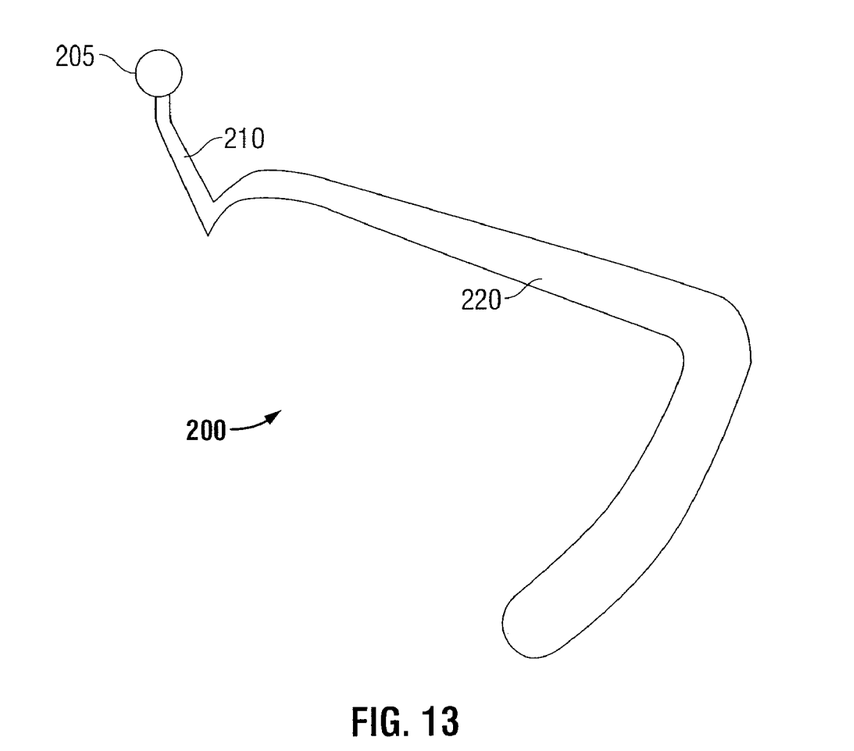
FIG. 13 is a side view of a tibial tunnel positioning guide according to yet another embodiment of the present disclosure.
Figure 14:
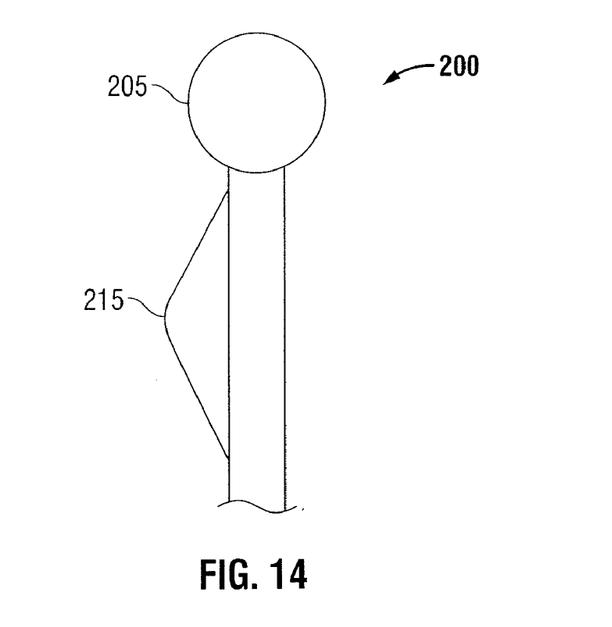
FIG. 14 is an enlarged side view of the distal end of the tibial tunnel positioning guide of FIG. 10.
Figure 15:
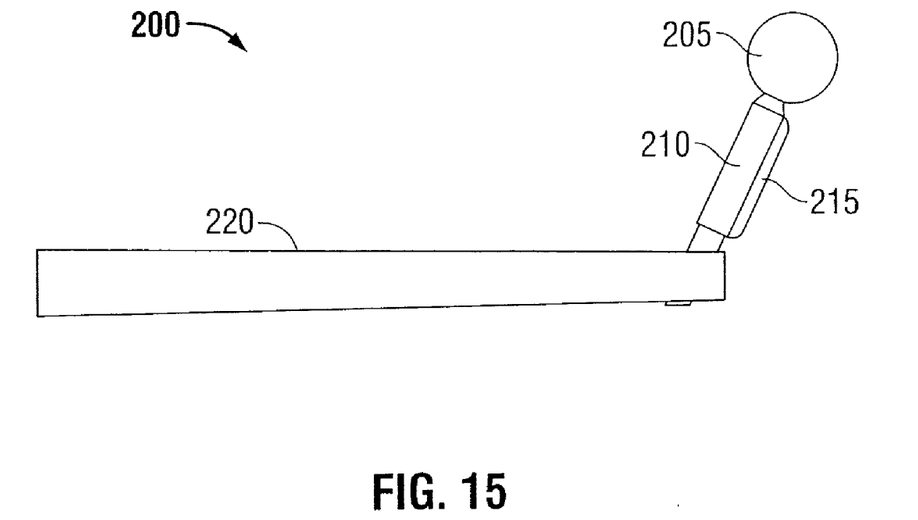
FIG. 15 is a side view of the distal end of the tibial tunnel positioning guide of FIG. 11.
Figure 16:
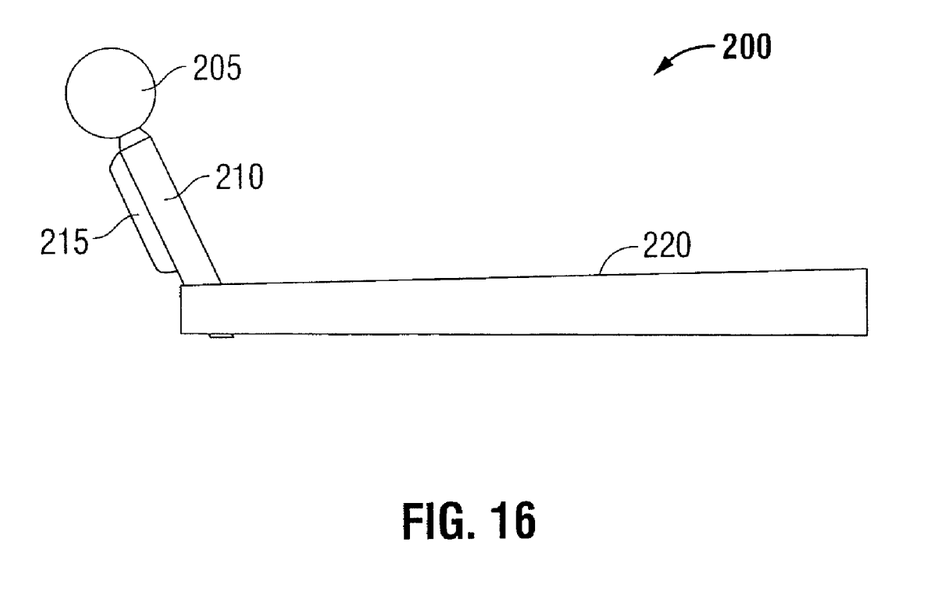
FIG. 16 is an alternate side view of the distal end of the tibial tunnel positioning guide of FIGS. 11 and 15.
Figure 17:
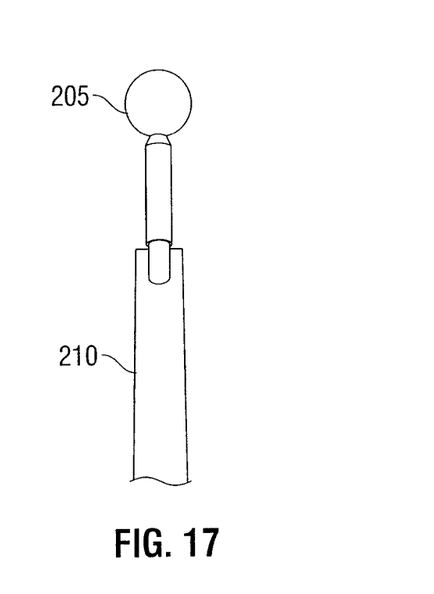
FIG. 17 is an end view of the distal end of the tibial tunnel positioning guide of FIGS. 11, 15 and 16.

Looking next at FIG. 8, still another guide references the roof of the intercondylar notch, as well as orienting the guide's position relative to the plane of the tibial plateau (U.S. Pat. No. 6,254,605, by Howell et al.). This referencing is done in an attempt to avoid impingement of the femoral roof by the graft ligament.

All of these prior art tibial tunnel positioning guides, while utilizing different referencing points and methods, still share the same overall approach: each of these guides is used to orient the tibial tunnel first, but in a position deemed appropriate for the femoral tunnel, which is thereafter drilled through that tibial tunnel. The limitations of such an approach is that the position of the tibial tunnel is often compromised in order to later drill an appropriate femoral tunnel. This often results in the tibial tunnel being placed in a position which is more posterior and more vertical than is anatomically desired.

Proper placement of the femoral tunnel is imperative in order for the ACL graft to be properly positioned on the femur. However, as a result of using the aforementioned trans-tibial technique, the position of the femoral tunnel is effectively dictated by the position of the first-drilled tibial tunnel. This often results in a femoral tunnel position, and thus, an ACL reconstruction (i.e., graft orientation, etc.) that is less than optimal.

In an attempt to better position the femoral tunnel, surgeons have recently begun utilizing the so-called "medial portal technique" to drill and create the femoral tunnel. An embodiment of a femoral drill guide for use in medial portal techniques is described in commonly owned patent application Ser. No. 12/366,967, the content of which are incorporated by reference in its entirety, and is shown generally as femoral guide 100 in FIG. 4. By drilling the femoral tunnel through the medial portal or an accessory portal, the femoral and tibial tunnels may be drilled independently of one another and, therefore, in a more appropriate anatomical position. While the medial portal approach greatly improves the ability of the surgeon to more accurately position the femoral tunnel, the older, simple trans-tibial guides are still used by the surgeon to position the tibial tunnel.

Therefore, it would be beneficial to have a device and method for orienting the position of a second-drilled tibial tunnel based on a first-drilled femoral tunnel. It would further be beneficial to have a device and method for positioning a tibial tunnel utilizing the medial portal approach prior to drilling a femoral tunnel.

SUMMARY

A device for positioning a tibial tunnel during ACL reconstruction is provided. The device includes a portion insertable into a pre-formed opening in the femur. The device may further include an elongated body having proximal and distal ends and an arm extending at an angle from the distal end of the elongated body, the arm being configured for insertion through a medial portal. The portion insertable into a pre-formed opening in the femur may include a tip formed on a distal end of the arm.

The elongated body of the positioning device may be arced. The arm may be configured to point to the position of the resulting tibial tunnel on a tibial plateau when the distal tip is disposed in a femoral tunnel. The arm may include a pointed elbow configured to point to the position of the resulting tibial tunnel on the tibial plateau/ACL footprint. The arm may be configured to orient the angle of the resulting graft in the sagittal plane. The arm may extend from elongated body at an angle from about fifty degrees (50°) to about sixty degrees (60°). The angle between the elongated body and the arm may be adjustable. The arm may include a lateral projection. The proximal end of the elongated body may be configured for connection to an outrigger. The outrigger may be configured to direct a guide wire through the tibial. Also provided is a method for positioning a tibial tunnel during ACL reconstruction. The method includes the steps of forming an opening in a femur bone, inserting a portion of a device into the opening, and using the device to position an opening in a tibia bone. The step of creating an opening in a femur bone may performed using a medial portal approach. The device may include an elongated body, an arm extending at an angle from a distal end of the elongated body, and a tip formed on a distal end of the arm, the tip being configured for insertion into the femoral tunnel. The method may further include the step of positioning the device by referencing at least one of a lateral wall of the femoral notch and one or more tibial spines.

The device may further include a lateral projection for referencing the femoral notch. The method may further include the step of adjusting the coronal medial/lateral orientation angle of the arm of the device in a way that mimics an intact ACL. The arm of the device may be configured for insertion through a medial portal. The method may further include the step of flexing the knee through a range of motion to check for resultant graft impingement. A proximal end of the arm may include an elbow for engaging the tibia.

Additionally provided is a method for positioning a tibial tunnel during ACL reconstruction. The method includes the steps of providing a tibial guide including an elongated body, an arm extending at an angle from a distal end of the elongated body, and a tip formed on a distal end of the arm, the tip including a point for engaging a femur, inserting the distal end of the elongated body into a knee joint using a medial portal approach, engaging the pointed tip with the femur in a position corresponding to that of a desired femoral tunnel, and positioning the tibial guide by referencing at least one of a lateral wall of the femoral notch and one or more tibial spines.

In accordance with various embodiments, the present invention may also provide a device for positioning a tibial tunnel during ACL reconstruction, the device comprising: a distal portion including a body and a distal arm extending from the distal end of the body, and an outrigger configured to be held by a user, the outrigger and the distal portion being selectively rotatable relative to each other such that the distal portion and the outrigger may be selectively moved out of alignment relative to each other when viewed from above. The outrigger may be selectively disconnectable from the distal portion. The distal portion may include a body and a distal tip, and the distal tip may be configured for insertion into a pre-formed opening in a femur.

The outrigger and the distal portion may be rotatably moveable to a position at which they are disposed at an angle of about thirty degrees (30°) relative to each other. At least one of the outrigger and the distal portion may include a physical stop for preventing the distal portion from being over-rotated relative to the outrigger. The distal portion may include a generally round proximal end that is configured to be rotatably received within a generally round receiving bore of the outrigger. At least one of the outrigger and the distal portion may include a locking feature for selectively locking the outrigger and the distal portion relative to each other. The locking feature may include a threaded bore on the outrigger, the threaded bore in communication with the receiving bore of the outrigger and configured to receive a set screw, the set screw being actuatable so as to selectively engage and lock into position the proximal end of distal portion within the receiving bore. At least one of the outrigger and the distal portion may include an indication feature for providing an indication to a user that the outrigger and the distal portion are in a particular orientation relative to each other. The indication feature may include a groove, a knurl, a protrusion or a detent for providing a tactile indication to a user that the outrigger and the distal portion are in a particular orientation relative to each other. At least one of the outrigger and the distal portion may include indicia for providing a visual indication to a user that the outrigger and the distal portion are in a particular orientation relative to each other. The indicia may include one or more of numbers, markings, symbols and arrows.

DETAILED DESCRIPTION OF THE EMBODIMENTS

Looking now at FIGS. 10-17, there is shown a tibial tunnel positioning guide 200. Tibial tunnel positioning device 200 generally includes a distal tip 205, an arm 210 and an arced body 220. Distal tip 205 is configured to reference a previously-drilled femoral tunnel (e.g., a femoral tunnel drilled using a medial portal approach). Distal tip 205 may be configured in any shape or size suitable to mate with the femoral tunnel. As shown, distal tip 205 is generally ball-tipped and includes a diameter of substantially the size of the previously-drilled femoral tunnel. Arm 210 extends proximally from distal tip 205 and connects distal tip 205 to arced body 220. Arm 210 is configured to point to the position of the resulting tibial tunnel on the tibial plateau when distal tip 205 is disposed in femoral tunnel 25. Arm 210 is further configured to orient the angle of the resulting graft in the sagittal plane. Studies have determined that, on average, an intact ACL exists in the sagittal plane at an angle of fifty-five degrees (55°) in reference to the perpendicular axis of the tibia (or the plane of the medial or lateral surface of the tibial plateau/joint surface). Accordingly, arm 210 is configured to connect distal tip 205 to body 220 at a pre-determined angle. Arm 210 may be configured to extend from body 220 at any predetermined angle, preferably from about fifty degrees (50°) to about sixty degrees (60°). This configuration allows a surgeon to choose a particularly-angled tibial tunnel positioning guide 200 based on MRI, X-ray or other imaging data. Alternatively, tibial tunnel positioning device 200 may be configured with an angle-adjustable arm (not shown) such that arm 210 may be adjusted to any angle required to meet the needs of the surgeon.

Arm 210 may further include a lateral projection 215. Lateral projection 215 is configured to reference the lateral wall of the femoral notch to help position the resulting tibial tunnel to avoid lateral wall impingement once the graft ligament is positioned. Lateral projection 215 also aids the surgeon in orienting the medial-lateral position of tibial tunnel 20 and its orientation angle in the coronal plane. In this manner, the surgeon may set the coronal medial/lateral orientation angle of the resultant graft position in a way that mimics an intact ACL. Arm 210 may also include a pointed "elbow" which points to the resulting tibial tunnel's guide wire position on the tibial plateau/ACL footprint.

Arced body 220 extends proximally from arm 210 and is configured to facilitate insertion through the medial portal. The configuration of arced body 220 accounts for medial portal positioning to avoid the position of the portal influencing guide placement. More particularly, arm 210 of tibial tunnel positioning guide 200 may be sized and shaped to mirror the size and shape of the ligament graft to be positioned. This allows the surgeon a visual reference of what the resulting graft will look like when placed in the knee. It should be appreciated that forming arm 210 to mirror the form of the ligament graft also allows the surgeon to check for any impingement prior to drilling tibial tunnel 20. For example, once tibial tunnel positioning guide 200 is docked into the pre-drilled femoral tunnel (i.e., by placing the distal ball tip in the femoral tunnel), the surgeon may bring the knee through a range of motion to check for resultant graft impingement before creating the tibial tunnel.

Figure 18:
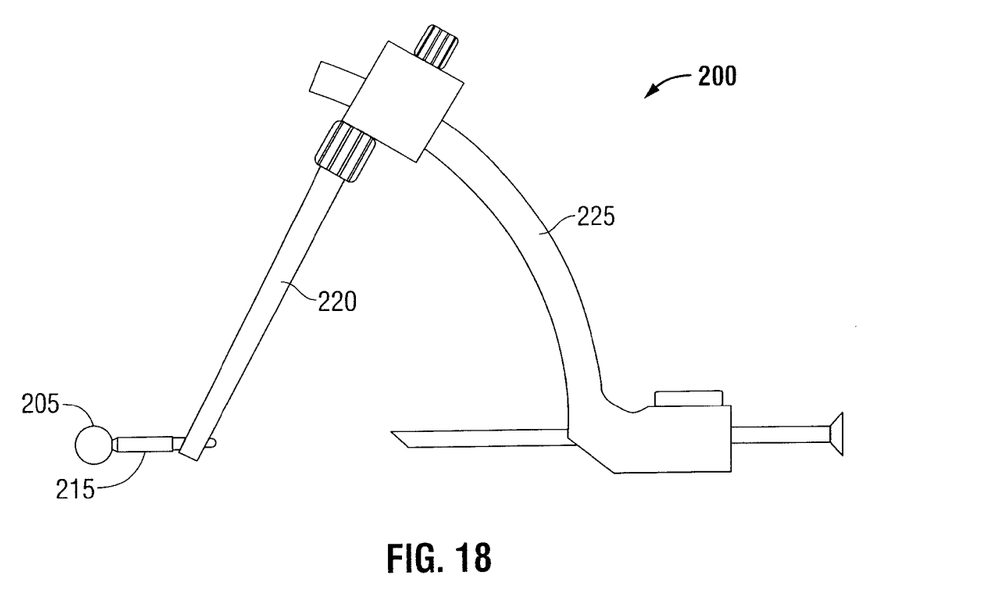
FIG. 18 is a side view of the tibial tunnel positioning guide of FIGS. 11 and 15-17 secured to an outrigger.

Arced body 220 may also be configured for connection to an outrigger 225. (FIG. 18). Outrigger 225 positions the guide wire to be drilled through starting point of the outer tibial cortex. Arced body 220 and outrigger 225 may join at a set angle, or an adjustable angle such that the resultant outer tibial cortex starting point is not positioned too far medially, and in the position desired by the surgeon. In other words, body 220 and/or arm 210 (and therefore distal tip 205) may be set off-angle or off-axis from outrigger 225 if desired.

Figure 19:
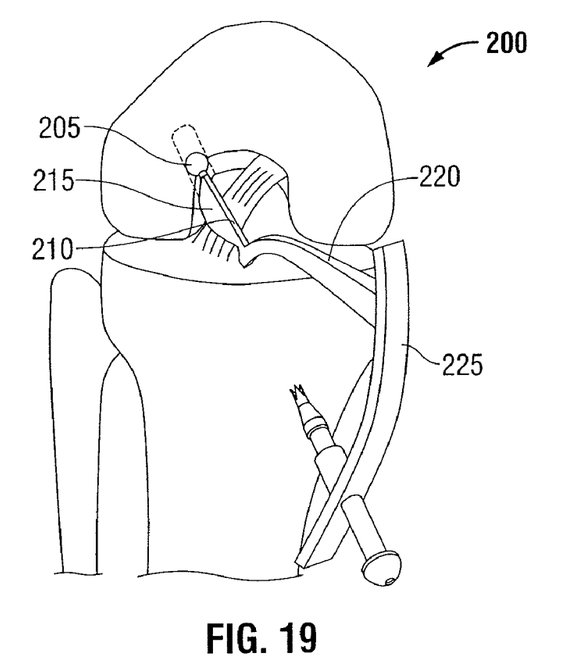
FIG. 19 is partial cut away view of a knee joint including a tibial tunnel positioning guide and outrigger of FIG. 18 positioning.
Figure 20:
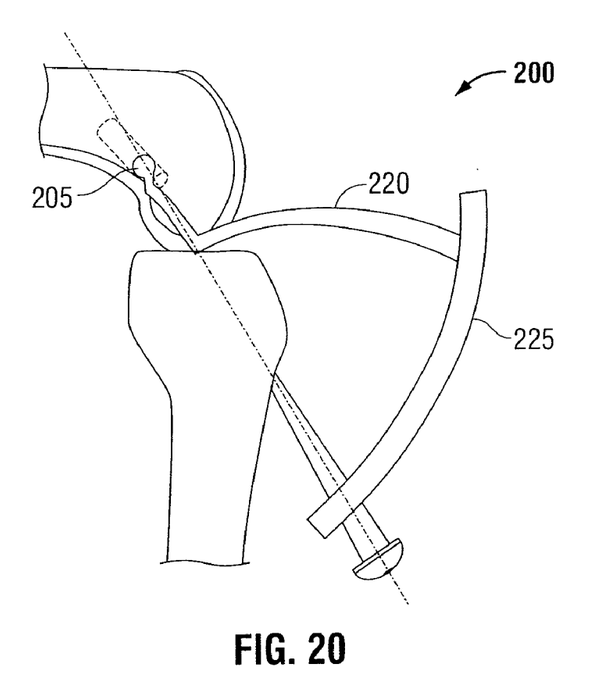
FIG. 20 is a partial cut-away side view of the knee joint of FIG. 19 illustrating the path of a guide wire through the tibia.
Figure 21:
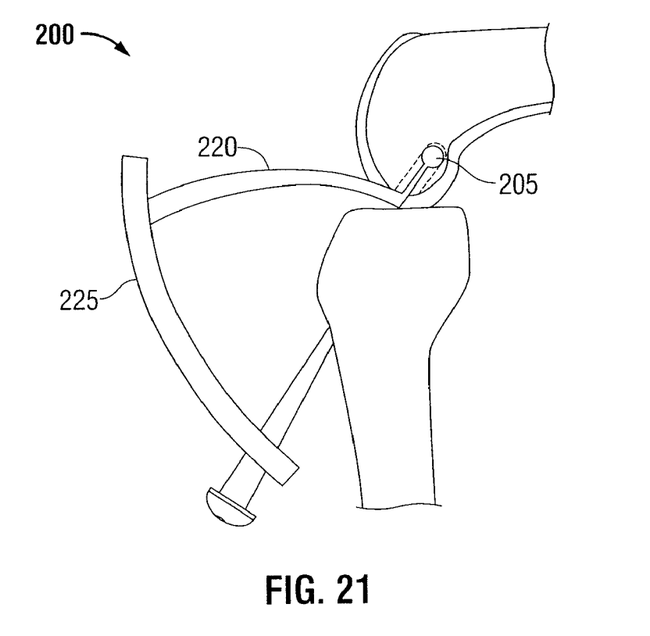
FIG. 21 is an alternate partial cut-away side view of the knee joint of FIGS. 19 and 20.

Looking next at FIGS. 19-21, tibial tunnel positioning guide 200 is placed through a medial portal with distal ball tip 205 of tibial tunnel positioning guide 200 positioned in the pre-drilled femoral tunnel. The anterior/posterior position of the resulting tibial tunnel is determined by selecting the angle of tibial tunnel positioning guide 200. The surgeon may do this in one of two ways: (i) by selecting an appropriately pre-angled guide, or (ii) by setting a desired angle on an angle-adjustable guide. The medial/lateral position of the guide (and therefore the resulting tibial tunnel) is determined by the lateral projection referencing the lateral wall of the notch. In addition, pointed elbow of arm 210 may also reference the tibial spines. In particular, the pointed elbow or arm 210 may reference the medial tibial spine to set the resultant graft in the proper anatomic coronal orientation.

Lastly, with an outrigger attached to tibial tunnel positioning guide 200, the surgeon may move the starting point of the tibial tunnel on the outer cortex, (e.g., medially and away from the MCL), if desired. With the aforementioned positions and references set, tibial tunnel positioning guide 200 is now in place so that the surgeon can confidently drill the tibial tunnel.

Figure 22:
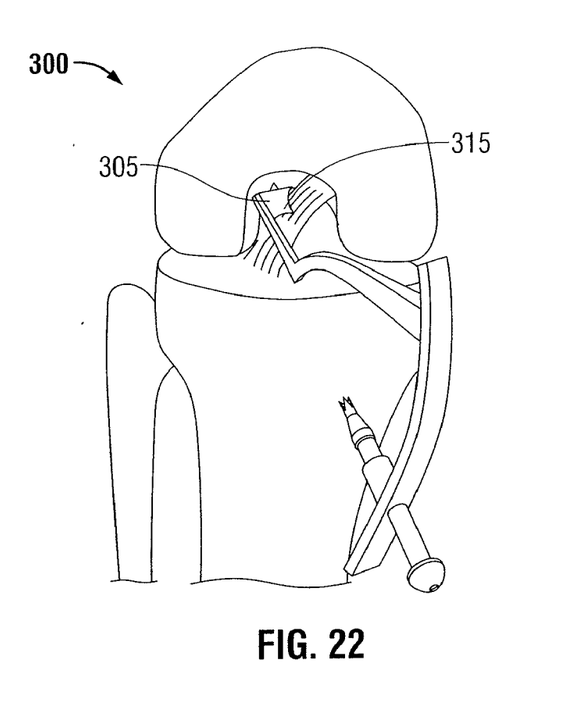
FIG. 22 is a perspective view of a knee joint including a tibial tunnel positioning guide according to still yet another embodiment of the present disclosure and further including an outrigger.

Looking now at FIG. 22, tibial tunnel positioning guide 300 may also be used in an approach where the femoral tunnel has not yet been drilled. In this embodiment, distal tip 305 is configured with a sharp point rather than a ball-tipped end, and a medial projection 315 rather than a lateral projection. The point of distal tip 305 and medial projection 315 are positioned referencing the location of where the PCL is inserted on the femoral notch. Tibial tunnel positioning guide may also be positioned with the point placed at any other spot along the femoral notch, or other position according to the preferences of the surgeon.

Figure 23:
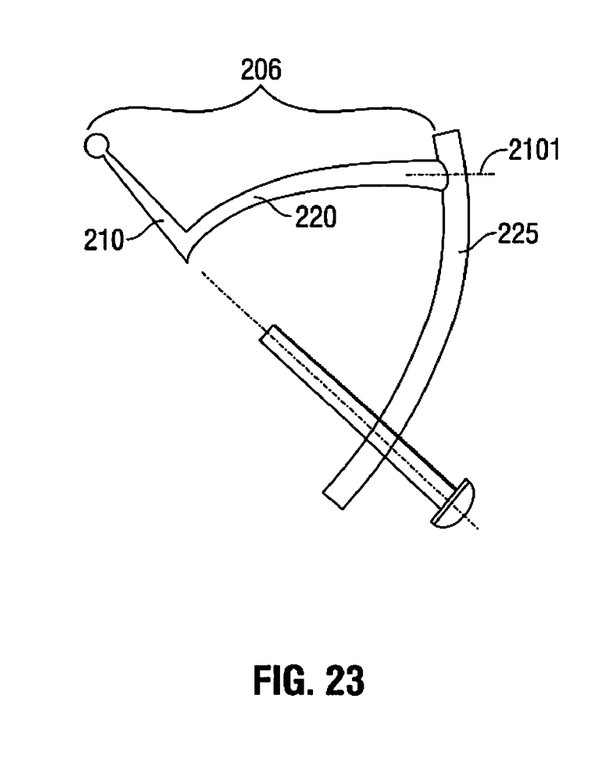
FIGS. 23 and 24 illustrate a tibial tunnel positioning device having disconnectable and/or rotatable components, according to still yet another embodiment of the present disclosure.
Figure 24:
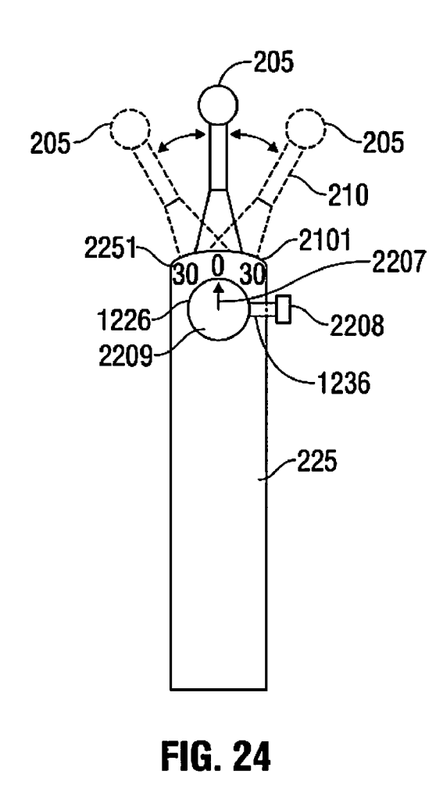

While some of the particular embodiments shown hereinabove have the outrigger 225 and the distal portion of the device, e.g., the body 220 and the arm 210, being integrally formed and/or rigidly connected to each other, it should be recognized that the present invention may also include other embodiments in which the outrigger 225 and the distal portion of the device, e.g., the body 220 and the arm 210, are not integrally formed or not rigidly connected to each other. For example, various embodiments of the present invention may include an arrangement in which the outrigger 225 and the distal portion of the device, e.g., the body 220 and the arm 210, are separate components that are moveable relative to each other. FIGS. 23 and 24 illustrate an example embodiment of a tibial tunnel positioning device 300 having an arrangement in which the outrigger 225 and the distal portion 206 of the device, e.g., the body 220 and the arm 210, are separate components that are disconnectable and/or rotatable relative to each other. Specifically, FIGS. 23 and 24 illustrate an example embodiment of the present invention having an arrangement in which the outrigger 225 is rotatably relative to and/or selectively disconnectable from the distal portion 206 of the device, e.g., the arm 210 and the body 220, at a pivot axis 2101.

Providing an arrangement in which the outrigger 225 and the distal portion 206 of the device, e.g., the body 220 and the arm 210, are separate components that are moveable, e.g., rotatably and/or selectively disconnectable, relative to each other may provide additional advantages as compared to embodiments in which the outrigger 225 and the distal portion of the device, e.g., the body 220 and the arm 210, are integrally formed and/or rigidly connected to each other. For example, and as described hereinabove, in embodiments in which the outrigger 225 and the distal portion 206 of the device, e.g., the body 220 and the arm 210, are integrally formed and/or rigidly connected to each other, the outrigger 225 and the distal portion 206 of the device are typically disposed so as to be aligned relative to each other when viewed from above. Specifically, when a surgeon utilizes a convention tibial tunnel positioning guide, e.g., in which the outrigger 225 and the distal portion 206 of the device are aligned relative to each other when viewed from above, the surgeon must change the position of the device during the surgical procedure, e.g., to account for whether he or she is performing the procedure on the patient's right knee or the left knee. In addition, when a surgeon utilizes a convention tibial tunnel positioning guide, e.g., in which the outrigger 225 and the distal portion 206 of the device are aligned relative to each other when viewed from above, the surgeon is limited to the size and shape of the distal portion 206 attached to the outrigger and can not change the distal portion 206 if he or she determines that the distal portion is undesirable or otherwise less than optimal.

In contrast, by providing an arrangement in which the outrigger 225 and the distal portion 206 of the device, e.g., the body 220 and the arm 210, are separate components that are moveable, e.g., rotatably and/or selectively disconnectable, relative to each other, a surgeon may selectively adjust the relative positions of the outrigger 225 and the distal portion 206 of the device so as to be misaligned relative to each other when viewed from above, thereby providing improved tunnel positioning. Furthermore, the surgeon need not change the position of the device during the surgical procedure to account for whether he or she is performing the procedure on the patient's right knee or the left knee, but rather may adjust the relative positions of the outrigger 225 and the distal portion 206 of the device so as to match the specific knee being worked on. In addition, by providing an arrangement in which the outrigger 225 and the distal portion 206 of the device, e.g., the body 220 and the arm 210, are separate components that are moveable, e.g., rotatably and/or selectively disconnectable, relative to each other, a surgeon is not limited to the size and shape of the distal portion 206 attached to the outrigger, but rather is able to change the distal portion 206 if he or she determines that the distal portion 206 is undesirable or otherwise less than optimal. Such movability, e.g., rotatability and/or selectively disconnectability, of the outrigger 225 and the distal portion 206 of the device may allow the surgeon to adjust the relative positions of the components, and thereby the position of the tibial tunnel, to accommodate variations in a surgeon's tunnel position preference, to accommodate different patients' anatomy, e.g., different size patients, to avoid PCL impingement, etc.

The present invention contemplates various ways in which a surgeon may cause the outrigger 225 and the distal portion 206 of the device 300 to move, e.g., rotate, between the first and second positions. For example, the tibial tunnel positioning device 300 may include a generally round proximal end 2209 that extends into a generally round bore 1226 as shown in FIG. 24. Of course, any shapes may be employed. Furthermore, any mechanical arrangement that moveably connects these components to each other may be employed.

The tibial tunnel positioning device 300 may also include selectively lockable features that, when unlocked, enable a surgeon to physically move the outrigger 225 relative to the distal portion 206 to a desired position, and when locked by the surgeon, prevent relative movement of the outrigger 225 and the distal portion 206. FIG. 24 illustrates an example embodiment of such selectively lockable features, including a threaded bore 1236 that is in communication, e.g., perpendicular, with the bore 1226. The threaded bore 1236 is configured to receive a set screw 2208 that may be actuated by a surgeon so as to selectively engage and lock into position the proximal end 2209 of the body 220 within the bore 1226. Of course, any type of selectively lockable features, e.g., biased pins that engage openings on the outer circumference of the proximal end 2209 of the body 220, clamps, etc., may be employed, whereby a surgeon may engage, e.g., loosen and tighten, such features as desired.

While the tibial tunnel positioning device 300 may be configured so as to enable the distal portion 206 to freely move, e.g., freely rotate, relative to the outrigger 225, it should be recognized that, in alternative embodiments, the tibial tunnel positioning device 300 may provide features that regulate, restrict or otherwise control the free movement of the distal portion 206 relative to the outrigger 225. For example, the tibial tunnel positioning device 300 may provide features that limit the range of motion of the distal portion 206 relative to the outrigger 225. Such a feature may include physical stops that prevent the distal portion 206 from being over-rotated relative to the outrigger 225. For example, either or both of the outrigger 225 and the body 220 may include one or more physical stops that contact each other when, e.g., the outrigger 225 and the body 220 are in a first relative position and/or when the outrigger 225 and the body 220 are rotated to a second relative position, and that prevent the outrigger 225 and the body 220 from being pivoted beyond the desired angles relative to each other. Such physical stops may be features that extend radially from the outrigger 225 and/or the body 220, e.g., corresponding nubs or shoulders.

While the tibial tunnel positioning device 300 may provide features that regulate or restrict the free movement of the outrigger 225 and the body 220 relative to each other by limiting the range of motion of the arm 210 and the body 220 relative to each other, it should be recognized that, additionally or alternatively, the tibial tunnel positioning device 300 may provide features that regulate or restrict the free movement of the outrigger 225 and the body 220 relative to each other by providing resistance to the movement of the outrigger 225 and the body 220 relative to each other. Such features may include grooves or knurls on one or more of the outrigger 225 and the body 220. Such features may generate increased friction between the outrigger 225 and the body 220 when moved, as compared to a relatively lower friction that would be present without such features. The friction generated by such features may be relatively low, such that there is little resistance needed to move the outrigger 225 and the body 220 relative to each other. Alternatively, such friction may be relatively high, such that, absent a force exerted by the surgeon, the outrigger 225 and the body 220 will remain in their relative positions. Such features may also include one or more of protrusions and/or detents on one or more of the outrigger 225 and the body 220. Such protrusions and/or detents may be located at specific positions of the outrigger 225 and/or the body 220. For example, in an embodiment, such protrusions and/or detents are located at specific positions of the outrigger 225 and/or the body 220 such that a surgeon will experience a tactile indication when the outrigger 225 and the body 220 are at specific positions relative to each other, e.g., when they are positioned 30° out of alignment in either the left or right directions as shown in FIG. 24. Of course, any number of features, e.g., protrusions and/or detents, indicating any number of relative positions of the outrigger 225 and the body 220, may be employed.

In addition, the tibial tunnel positioning device 300 may provide indicia that provide an indication to the surgeon of the position of the outrigger 225 and the body 220 relative to each other. Such indicia, an example of which is shown in FIG. 24, may indicate specific relative positions of the outrigger 225 and/or the body 220. For example, in the embodiment shown in FIG. 24, such indicia 226 may be located at specific positions of the outrigger 225 and/or the body 220, e.g., at positions of 30° out of alignment in either the left or right directions as shown in FIG. 24, such that a surgeon will be able to select the relative positions of the outrigger 225 and the body 220. Of course, any type of indicia 226, e.g., numbers, markings, symbols, arrows, etc., indicating any number of relative positions of the outrigger 225 and the body 220, may be employed. In the embodiment shown in FIG. 24, the indicia include an arrow 2207 located on the proximal face of the proximal end 2209 of the body 220, the arrow 2207 being aligned with the distal portion 206. In addition, the indicia include numerical markings 2251 provided on the outrigger 225. In this case, the numerical markings 2251 correspond to an angle between the distal portion 206 and the outrigger 225. In order to place the outrigger 225 and the body 220 at a desired angle relative to each other, the surgeon simply moves these components until the arrow 2207 points to the numerical marking corresponding to the desired angle. Furthermore, such indicia may be located at specific positions of the outrigger 225 and/or the body 220 that coincide with the specific positions of protrusions and/or detents of the outrigger 225 and/or the body 220, thus providing a surgeon with both a visual and a tactile indication when the outrigger 225 and the body 220 are at specific positions relative to each other.

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A device for identifying a desired location of a tibial tunnel during ACL reconstruction, the device comprising:
    a body;
    an arm extending from a distal end of the body, wherein a distal end of the arm is configured for insertion into a pre-drilled opening in a femur and a proximal end of the arm is configured to engage a tibia at a desired location of the tibial tunnel; and
    an outrigger including a curved portion and a tibial drill guide, wherein a proximal end of the body is rotatably supported within a receiving bore formed on the curved portion of the outrigger and is configured such that the proximal end of the arm remains disposed along a central axis defined by the tibial drill guide throughout rotation of the body about a longitudinal axis of the body, wherein the body includes a locking feature for selectively locking the outrigger and the body relative to each other, wherein the locking feature includes a threaded bore on the outrigger formed orthogonal to the longitudinal axis of the body, the threaded bore being in communication with the receiving bore of the outrigger and configured to receive a set screw, the set screw being actuatable so as to selectively engage and lock into position the proximal end of body within the receiving bore.

2. The device of claim 1, wherein at least one of the outrigger and the body include an indication feature for providing an indication to a user that the outrigger and the body are in a particular rotational orientation relative to each other.

3. The device of claim 1, wherein the outrigger is selectively disconnectable from the proximal end of the body.

4. The device of claim 1, wherein the outrigger and the body are rotatably moveable to a position at which the outrigger and arm are disposed at an angle of about thirty degrees (30°) relative to each other.

5. The device of claim 1, wherein at least one of the outrigger and the body include a physical stop for preventing the body from being over-rotated relative to the outrigger.

6. The device of claim 1, wherein the body includes a generally round proximal end that is configured to be rotatably received within a generally round receiving bore of the outrigger.

7. The device of claim 6, wherein at least one of the outrigger and the body include an indication feature for providing an indication to a user that the outrigger and the body are in a particular orientation relative to each other.

8. The device of claim 7, wherein the indication feature includes a groove, a knurl, a protrusion or a detent for providing a tactile indication to a user that the outrigger and the body are in a particular orientation relative to each other.

9. The device of claim 6, wherein at least one of the outrigger and the body include indicia for providing a visual indication to a user that the outrigger and the body are in a particular orientation relative to each other.

10. The device of claim 9, wherein the indicia include one or more of numbers, markings, symbols and arrows.

11. The device of claim 1, wherein the distal end of the arm includes a spherical-shaped member.

12. The device of claim 11, wherein the spherical-shaped member includes a diameter substantially equal to the diameter of a femoral tunnel.

* * * * *